(12) United States Patent
Perren et al.

(10) Patent No.: US 6,736,818 B2
(45) Date of Patent: May 18, 2004

(54) RADIALLY EXPANDABLE INTRAMEDULLARY NAIL

(75) Inventors: Stephan Perren, Davos Dorf (CH); Markus Hehli, Frauenkirch (CH)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 10/141,835

(22) Filed: May 10, 2002

(65) Prior Publication Data
US 2002/0165544 A1 Nov. 7, 2002

Related U.S. Application Data

(63) Continuation of application No. PCT/CH99/00532, filed on Nov. 11, 1999.

(51) Int. Cl.[7] .............................................. A61B 17/58
(52) U.S. Cl. .............................. 606/63; 606/62; 606/60
(58) Field of Search ............................. 606/63, 60, 62, 606/66, 67, 68, 72

(56) References Cited

U.S. PATENT DOCUMENTS

| | | | |
|---|---|---|---|
| 2,834,342 A | 5/1958 | Yost | 128/92 |
| 3,002,514 A | 10/1961 | Deyerle | 128/92 |
| 3,025,853 A | 3/1962 | Mason | 128/92 |
| 3,029,811 A | 4/1962 | Yost | 128/92 |
| 3,561,437 A | 2/1971 | Orlich | 128/92 |
| 3,986,504 A | * 10/1976 | Avila | 606/63 |
| 4,055,172 A | 10/1977 | Ender et al. | 128/92 BC |
| 4,204,531 A | * 5/1980 | Aginsky | 606/63 |
| 4,262,665 A | * 4/1981 | Roalstad et al. | 606/62 |
| 4,483,335 A | 11/1984 | Tornier | 128/98 BC |
| 4,628,923 A | 12/1986 | Medoff | 128/92 |
| 4,667,663 A | 5/1987 | Miyata | 128/92 YZ |
| 4,776,330 A | 10/1988 | Chapman et al. | 128/92 |
| 4,908,032 A | 3/1990 | Keller | 623/18 |

(List continued on next page.)

FOREIGN PATENT DOCUMENTS

| | | |
|---|---|---|
| DE | 587 317 | 10/1933 |
| DE | 38 35 682 A1 | 4/1990 |
| EP | 0 086 552 A1 | 8/1983 |
| EP | 0 094 039 A1 | 11/1983 |
| GB | 2268068 | 1/1994 |
| SU | 1071298 A | 2/1984 |
| SU | 1337074 A1 | 9/1987 |
| WO | WO 97/18769 | 5/1997 |
| WO | WO 98/05263 | 2/1998 |

OTHER PUBLICATIONS

W. L. Pugh, "A Self–Adjusting Nail–Plate for Fractures About the Hip Joint," J. Bone Joint Surg. 37–A:1085–93, (1955).
Richards et al., "The AO Dynamic HIP Screw and the Pugh Sliding Nail in Femoral Head Fixation," J. Bone Joint Surg. [Br] 72–B:794–6, (1990).
Jarrett et al., "The stable internal fixation of peritrochanteric hip fractures," Part V (pp. 203–218).
Calandruccio et al., "Internal Fixation Devices for Fractures of the Proximal Femur American Academy of Orthopaedic Surgeons Committee on the History of Orthopaedic Surgery," Brochure (pp. 1–7).
William K. Massie, M.D., "Extracapsular Fractures of the Hip Treated by Impaction Using a Sliding Nail–plate Fixation," Chapter 18 (pp. 180–201).

*Primary Examiner*—Cary E. O'Connor
*Assistant Examiner*—Candice C. Melson
(74) *Attorney, Agent, or Firm*—Jones Day (57) ABSTRACT

The invention is related to an intramedullary nail for fixation of a fractured bone having a medullary canal. The intramedullary nail may comprise a first radially expandable section provided in a proximal section adjacent to the head of the intramedullary nail, a second radially expandable section provided in the distal section adjacent to the tip of the intramedullary nail, and a non-expandable middle section provided between said two radially expandable sections of the intramedullary nail. The head may provide a distraction mechanism, by means of which said two radially expandable sections are distractible transverse to said longitudinal axis.

33 Claims, 8 Drawing Sheets

U.S. PATENT DOCUMENTS

| | | | |
|---|---|---|---|
| 4,915,092 A | 4/1990 | Firicá et al. | 606/67 |
| 4,978,349 A | 12/1990 | Frigg | 606/67 |
| 5,002,544 A | 3/1991 | Klaue et al. | 606/69 |
| 5,032,125 A | 7/1991 | Durham et al. | 606/62 |
| 5,034,012 A | 7/1991 | Frigg | 606/62 |
| 5,047,029 A | 9/1991 | Aebi et al. | 606/61 |
| 5,053,035 A | 10/1991 | McLaren | 606/67 |
| 5,116,336 A | 5/1992 | Frigg | 606/65 |
| 5,133,718 A | 7/1992 | Mao | 606/69 |
| 5,281,225 A * | 1/1994 | Vicenzi | 606/62 |
| 5,295,991 A | 3/1994 | Frigg | 606/62 |
| 5,300,074 A | 4/1994 | Frigg | 128/67 |
| 5,312,402 A | 5/1994 | Schläpfer et al. | 606/53 |
| 5,437,666 A | 8/1995 | Tepic et al. | 606/55 |
| 5,443,466 A | 8/1995 | Shah | 606/62 |
| 5,462,547 A | 10/1995 | Weigum | 606/65 |
| 5,498,264 A | 3/1996 | Schlapfer et al. | 606/72 |
| 5,501,684 A | 3/1996 | Schlapfer et al. | 606/73 |
| 5,514,137 A | 5/1996 | Coutts | 606/62 |
| 5,534,001 A | 7/1996 | Schlapfer et al. | 606/61 |
| 5,591,168 A | 1/1997 | Judet et al. | 606/65 |
| 5,618,286 A | 4/1997 | Brinker | 606/60 |
| 5,741,256 A | 4/1998 | Bresina | 606/62 |
| 6,187,007 B1 | 2/2001 | Frigg et al. | 606/72 |
| 6,231,576 B1 | 5/2001 | Frigg et al. | 606/62 |

* cited by examiner

RADIALLY EXPANDABLE INTRAMEDULLARY NAIL

CROSS-REFERENCE TO RELATED APPLICATIONS

This application is a continuation of the U.S. national stage designation of copending International Patent Application PCT/CH99/00532, filed Nov. 11, 1999, the entire content of which is expressly incorporated herein by reference thereto.

FIELD OF THE INVENTION

The present invention relates generally to orthopaedic fixation devices, and in particular to a fixation system for bones having an intramedullary canal.

BACKGROUND OF THE INVENTION

Various types of intramedullary nails are already known in the state of the art, which are expandable in a limited section of the nail in order to allow the fixation of the nail against the bone cortex, e.g. by means of radially deploying a number of blades in the distal portion of the intramedullary nail. These devices, however, when in use may lead to clinical results that are not optimally consistent with the state of the art concept of fracture treatment. For instance, an intramedullary nail which is not extrafocal may negatively affect endosteal vascularisation in the fracture area because the largest expansion of the nail is in the fracture area. Also, the largest expansion of the nail in the fracture area may generate forces which may have the tendency to separate fragments in comminuted fractures or, in the case of longitudinal non-dislocated fractures to increase the gap and to dislocate fragments which may lead to loosening of the fixation. Thus, despite these developments, a need exists for a nail having expandable parts which may be located extrafocally, leaving the fracture area less affected from radial forces. Such a nail might be particularly strong in the middle part—between the proximal and distal sections—of the nail and might not require the use of fluoroscopy for distal nor proximal locking.

SUMMARY OF THE INVENTION

The invention in one embodiment is related to an intramedullary nail having a head, a tip, and a longitudinal axis for fixation of a fractured bone having a medullary canal. The intramedullary nail may comprise a hollow cylindrical sleeve extending along the longitudinal axis and surrounding a locking element coaxially to the longitudinal axis. The nail may further include a first radially expandable section adjacent to the head, a second radially expandable section adjacent to the tip, and a non-expandable section disposed between the first and second radially expandable sections. The head of the intramedullary nail may be provided with a distraction mechanism, by means of which the first and second radially expandable sections are distractible transverse to said longitudinal axis. The non-expandable section may comprise at least one unslotted tubular piece. In one embodiment of the intramedullary nail the non-expandable section has a length in the range of 10 to 25 mm. In another embodiment, the non-expandable section of the intramedullary nail has a length in the range of about 15 mm to about 22 mm.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto.

FIGS. 1–4 show a first embodiment of the invention which comprises a solid nail core 10 with a head 1 and a tip 2 and a longitudinal axis 3. In the proximal section 4 adjacent to head 1 a thread 9 is provided. The middle section 8 of core 10 has a smooth surface 13 and a diameter tapering towards the distal section 6 adjacent to tip 2. The middle section 8 of core 10 and the end section 11 of the core 10 are separated by an annular abutment 12, and end section 11 has a larger diameter than middle section 8.

Figure 1:
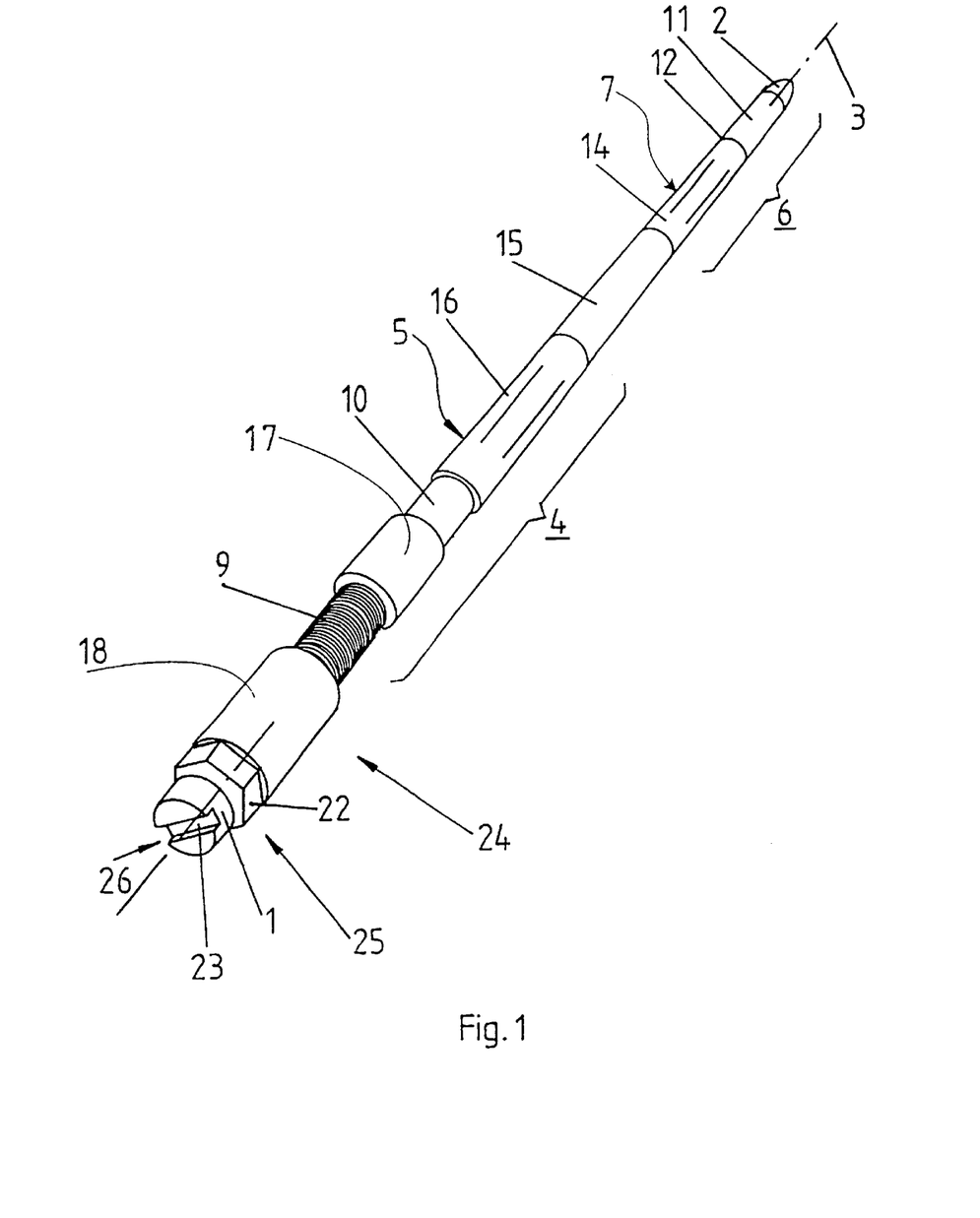
FIG. 1 shows a schematic representation of an intramedullary nail of the present invention in the non-expanded state.
Figure 2:
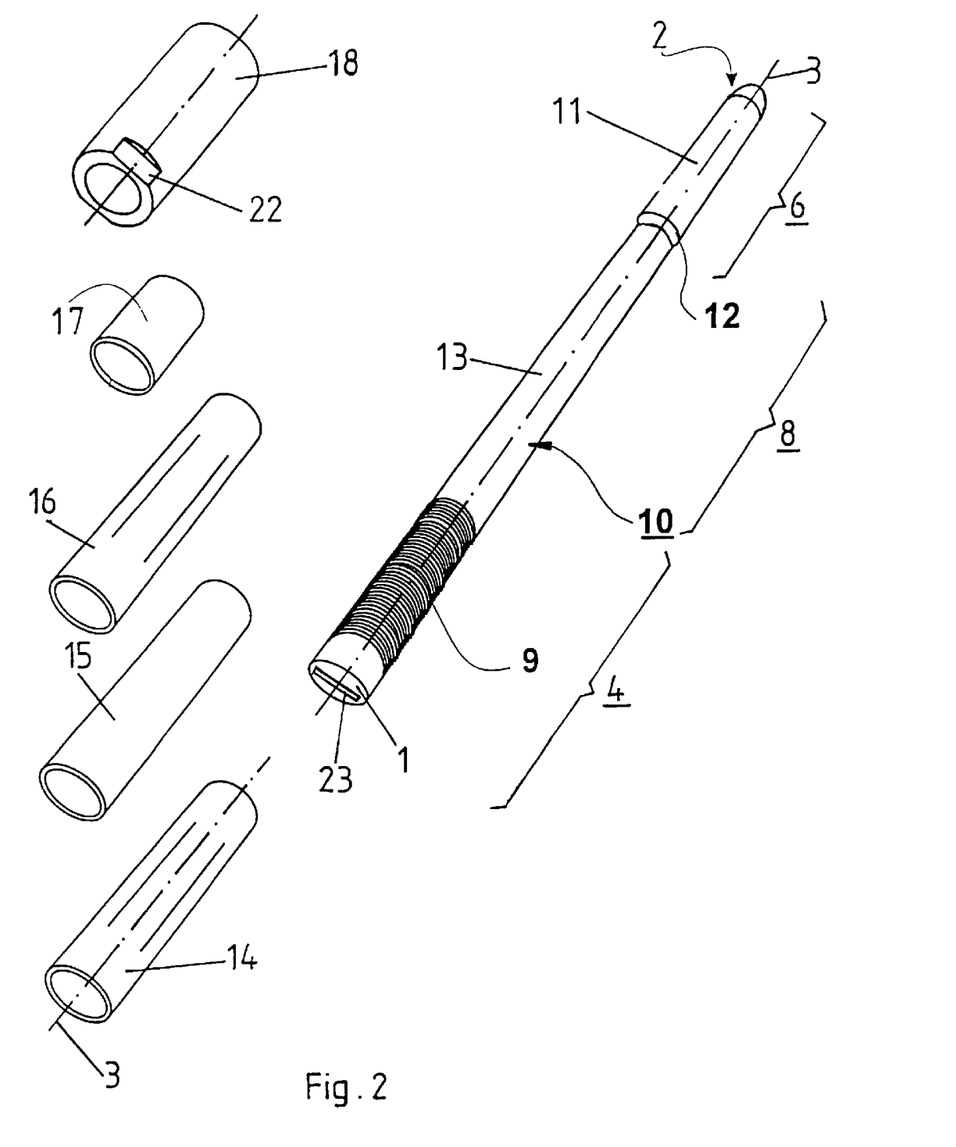
FIG. 2 shows an exploded view of the intramedullary nail according to FIG. 1.
Figure 3:
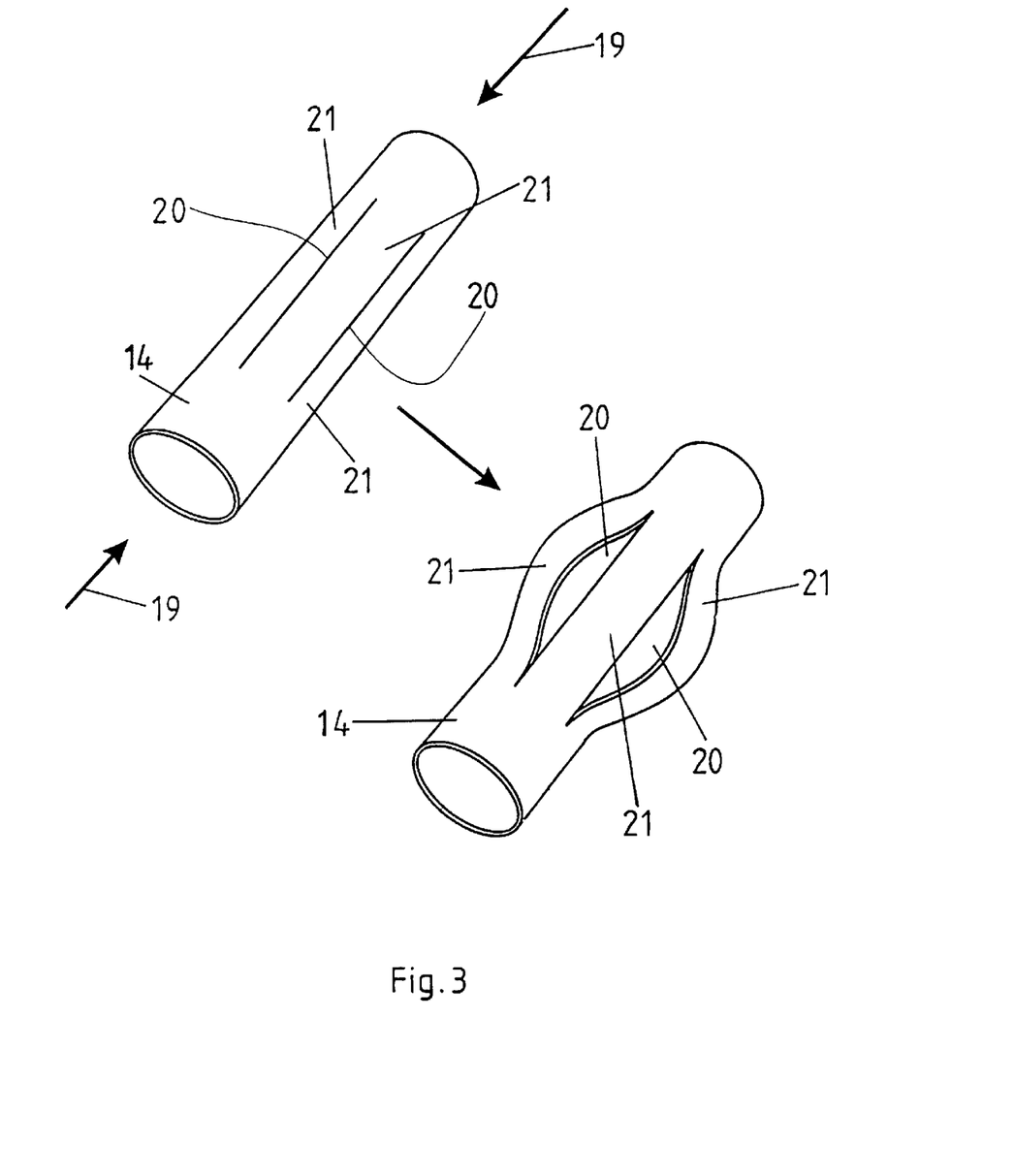
FIG. 3 shows a schematic representation of one of the expandable sections of the intramedullary nail of FIG. 1 in the non-expanded and in the expanded state.

As shown in FIG. 2, the following elements are slid over core 10 in the following sequence: a slotted tubular piece 14; an unslotted tubular piece 15; a slotted tubular piece 16; an unslotted tubular piece 17; and, a nut 18 with an inner thread corresponding with thread 9. When these elements are aligned on core 10, a screwing of nut 18—by means of the two parallel sides or hexagonal sides 22—on thread 9 and counter holding the core 10—by means of slot 23—will produce an axial force or compression (as indicated by arrows 19 in FIG. 3) on tubular pieces 17,16,15,14 as the slotted tubular piece 14 abuts against abutment 12 of core 10. As shown in FIG. 3, the cuts 20 of slotted tubular piece 14—as well as those of slotted tubular piece 16—will cause an expansion of slotted tubular piece 14 by radially deforming the belts 21 located between the cuts 20.

Figure 4:
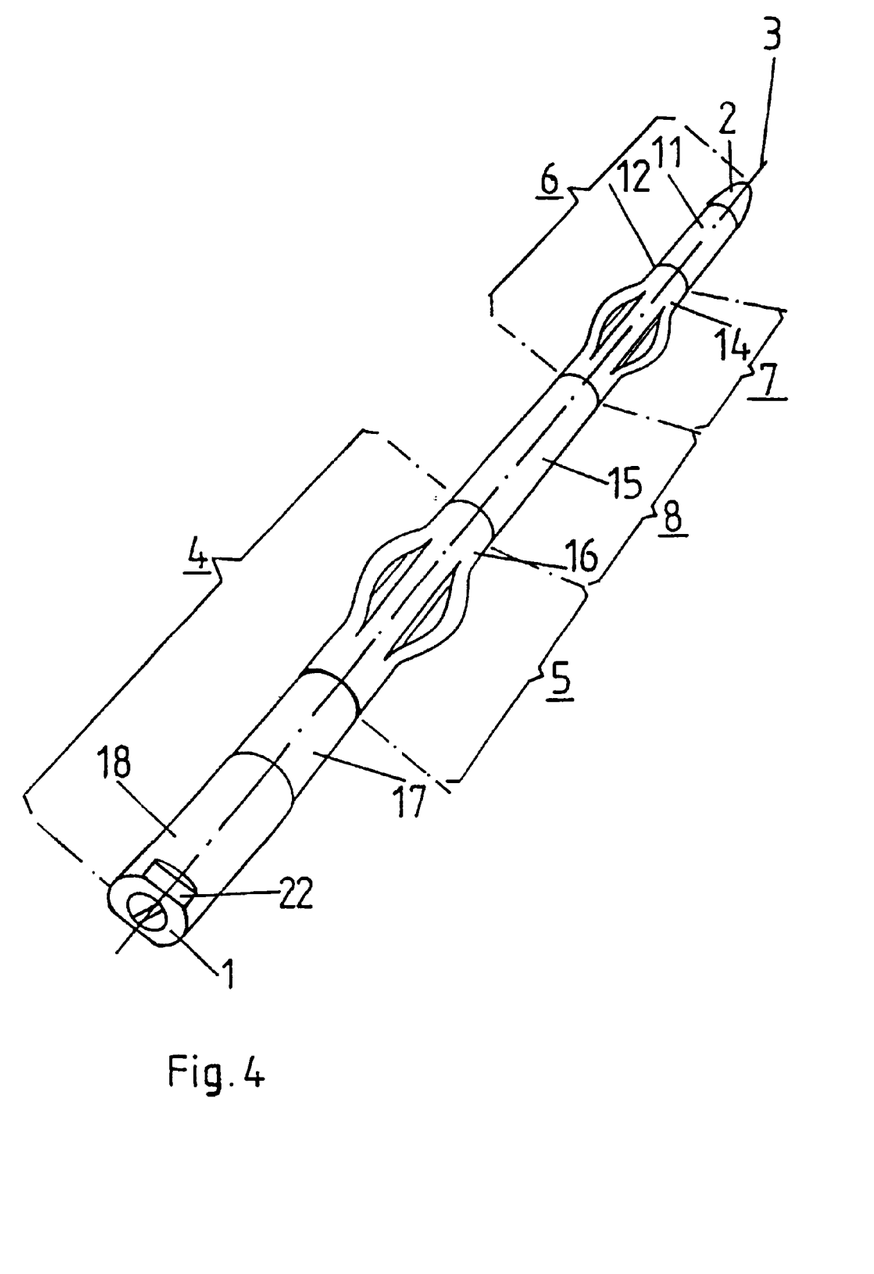
FIG. 4 shows a schematic representation of an intramedullary nail of the present invention in the expanded state.

As shown in FIG. 4, the nail is expandable at a first radially expandable section 5 in proximal section 4 adjacent to head 1 of the nail and in a second radially expandable section 7 in distal section 6 adjacent to tip 2 of the nail. In an alternate embodiment, instead of the two parallel sides or hexagonal sides 22 and the slot 23 for tightening the nut 18, two hexagon sockets may be placed.

Figure 5:
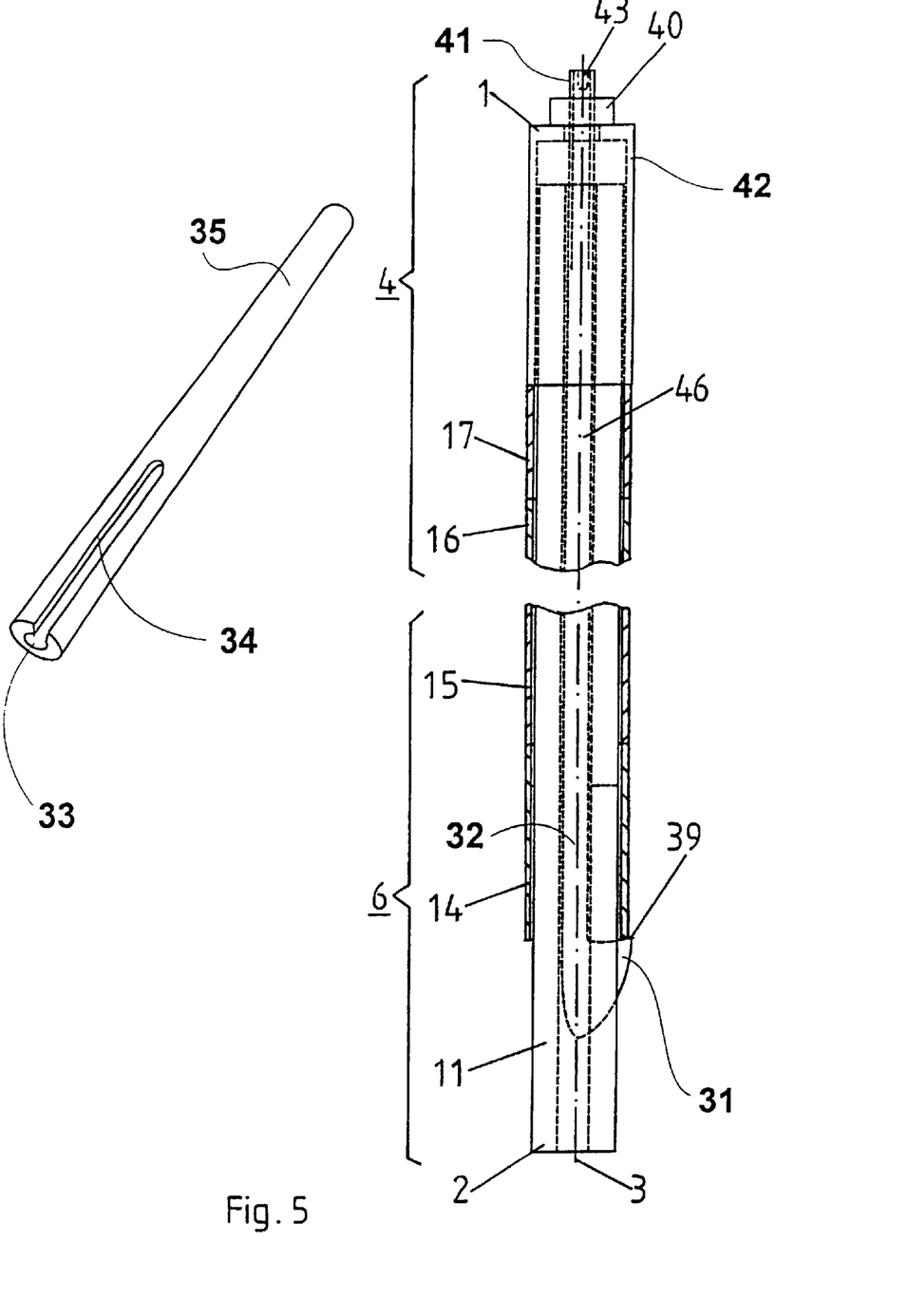
FIG. 5 shows a second embodiment of an intramedullary nail of the present invention in the non-expanded state.
Figure 6:
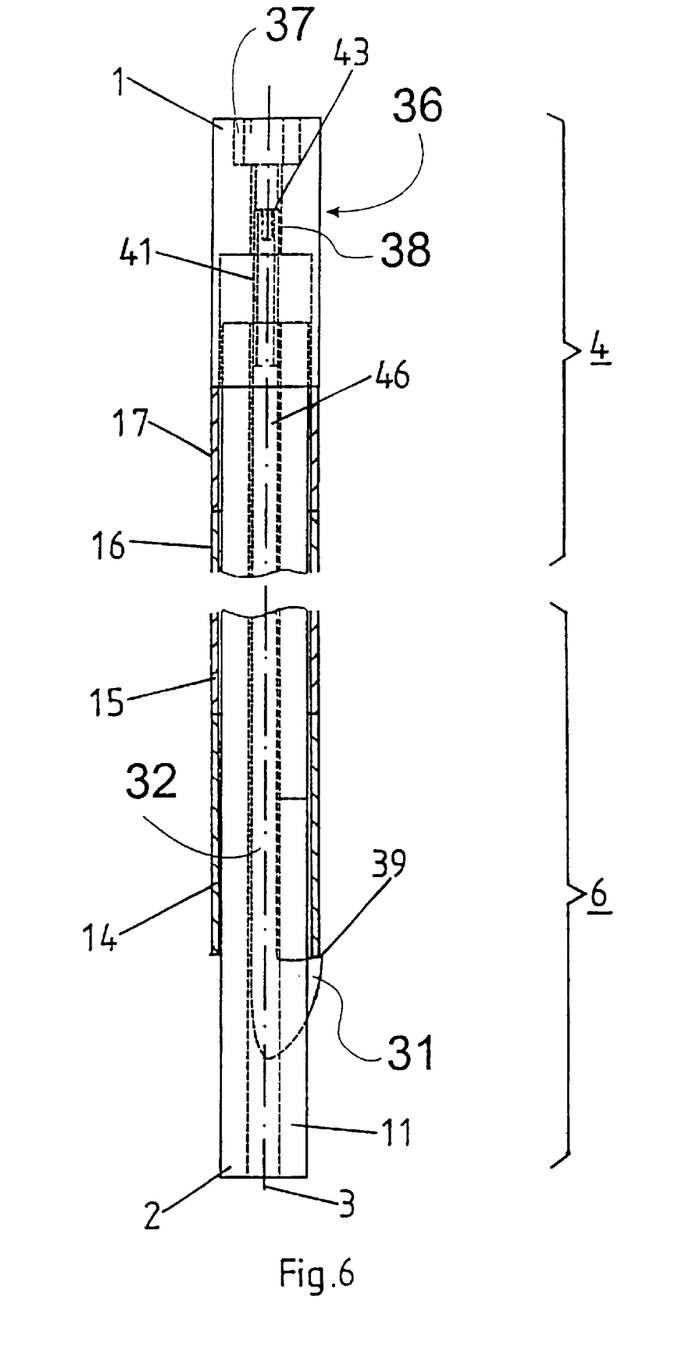
FIG. 6 shows a variation of the nut to be used with the intramedullary nail of FIG. 5.

FIG. 5 and FIG. 6 show a second embodiment of the intramedullary nail different from the embodiment shown in FIGS. 1–4, and it provides instead of the core 10, a hollow cylindrical sleeve 35 extending along the longitudinal axis 3 and surrounding a locking element 32 coaxially to longitudinal axis 3. The locking element 32 comprises a shaft with a thread 41 in the proximal section 4, and in distal section 6, a projection 31 forming an abutment 39. In the distal section 6 of sleeve 35, a slot 34 is provided penetrating the side wall through to bore 33 such that projection 31 of locking element 32 may slide within slot 34 in the direction of the longitudinal axis 3. The following elements are slid over sleeve 35 in the following sequence: a slotted tubular piece 14; an unslotted tubular piece 15; a slotted tubular piece 16; an unslotted tubular piece 17; an end cap 42; and, a nut 40 with an inner thread corresponding with thread 41.

Once these elements are aligned on sleeve 35 the tightening of nut 40 on thread 41 while counter holding locking element 32, by means of the hexagon socket 43, axially compresses the tubular pieces 14,15,16,17 as the slotted tubular piece 14 abuts against abutment 39 formed by the projection 31 of locking element 32. As described above in the first embodiment, belts 21 of the slotted tubular pieces 14,16 buckle and radially expand under the axial forces 19 (FIG. 3). In an alternative embodiment, instead of nut 40 and end cap 42, another end cap 36 providing interior thread 38 corresponding with thread 41 and a hexagon socket 37 may be used (FIG. 6).

Figures 7, 8:
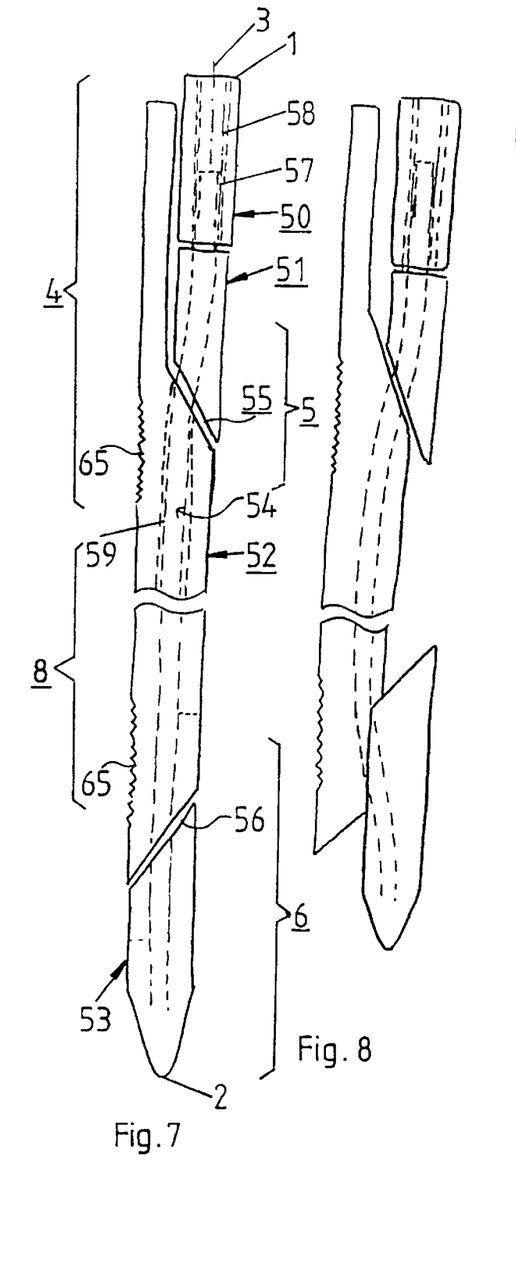
FIG. 7 shows a third embodiment of an intramedullary nail of the present invention and in the non-expanded state.
FIG. 8 shows the intramedullary nail of FIG. 7 in the expanded state.
Figure 9:
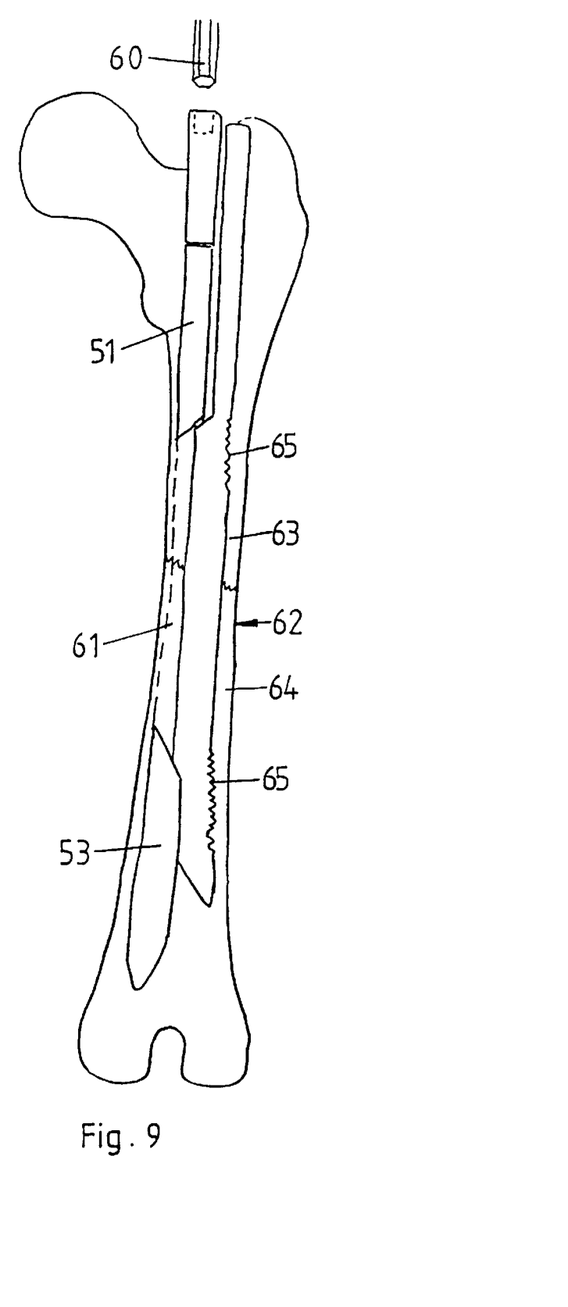
FIG. 9 shows the intramedullary nail of FIG. 7 implanted in a femur bone and in the expanded state

FIGS. 7–9 show a third embodiment of the intramedullary nail which basically comprises five elements: a nut 50, a hollow proximal section 51, a hollow middle section 52 and a hollow distal section 53 and a central wire 54. Contact between proximal section 51 and middle section 52 is represented by transverse abutments 55 (relative to the longitudinal axis 3). Contact between middle section 52 and distal section 53 is represented by transverse abutments 56 (relative to the longitudinal axis 3). Central wire 54 is fixed in distal section 53 and runs through the hollow channel 59 of sections 51,52,53. At its proximal end, central wire 54 has threads 57 which correspond to the interior threads 58 of nut 50. When the nut 50 is turned by means of a key 60, the central wire 54 is tightened and produces sliding of the proximal section 51 and distal section 53 on the transverse abutments 55 and 56 respectively. If the intramedullary channel 61 of the femur 62 (FIG. 9) is larger in diameter than the intramedullary nail, the proximal section 51 and distal section 53 will expand radially until firm fixation of the bone fragments 63 and 64. This radial expansion is possible because the transverse abutments 55,56 enclose an angle of between 5° and 85° with the longitudinal axis 3 such that upon applying a force in the axial direction by means of tightening nut 50, the proximal section 51, middle section 52, and the distal section 53 slide on abutments 55,56. Because the abutments 55,56 enclose an angle with the longitudinal axis 3 the sections 51;52;53 opposing each other at one abutment 55;56 each provide a sliding component orthogonal to the longitudinal axis 3 what causes a radial expansion of the intramedullary nail. The sharp radial teeth 65 in middle section 52 prevent axial displacement of the bone fragments 63,64 after its fixation.

Figure 10:
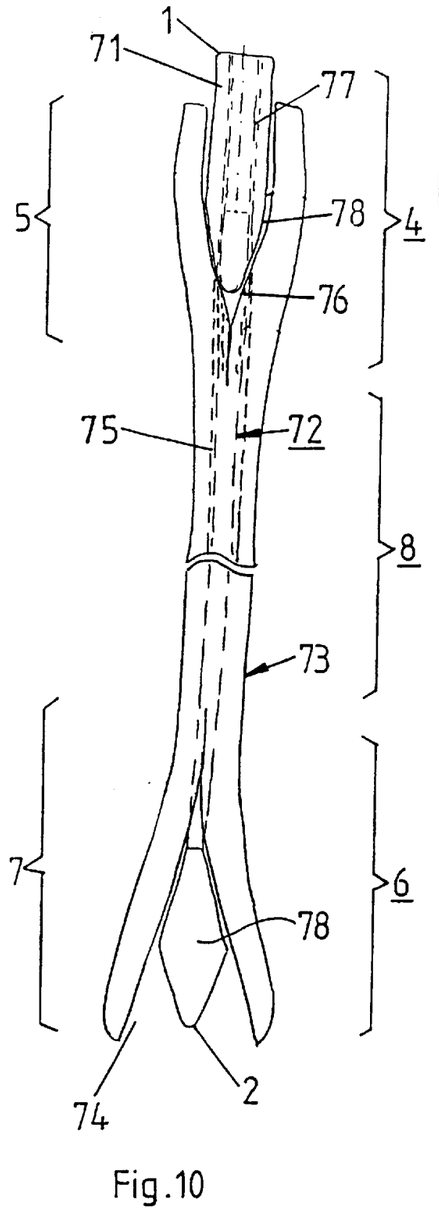
FIG. 10 shows a fourth embodiment of an intramedullary nail of the present invention in the expanded state.
Figure 11:
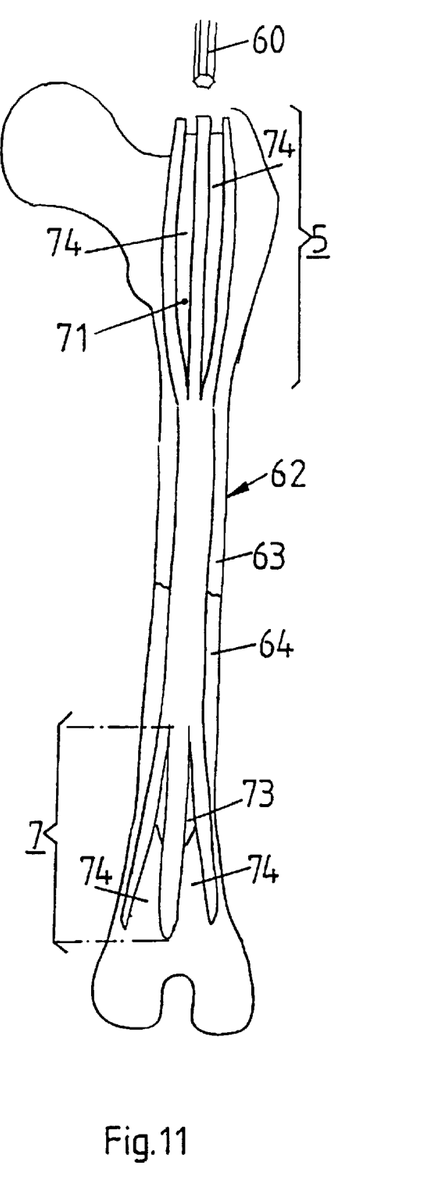
FIG. 11 shows a the intramedullary nail of FIG. 10 implanted in a femur bone and in the expanded state.

FIG. 10 and FIG. 11 show a fourth embodiment of the intramedullary nail which basically comprises three elements: a nut 71 with head 1 and conical tip 78, a central wire 72 with a cone like distal end 73, and a hollow intramedullary nail 73. The ends of intramedullary nail 73 are provided with a plurality of cuts 74. Central wire 72 runs through the hollow channel 75 of intramedullary nail 73 and—at its proximal end—has threads 76 which correspond to the interior threads 77 of nut 71. When nut 71 is turned by means of a key 60, the distance between the conical tip 78 of nut 71 and the cone-like distal end 73 of central wire 72 is shortened, so that cuts 74 of intramedullary nail 73 are expanded as shown in FIG. 11. The expansion of intramedullary nail 73 proximally and distally at sections 5 and 7 produces a firm fixation of the bone fragments 63 and 64 of femur 62.

The intramedullary nail may comprise a first radially expandable section provided in the proximal section adjacent to the head of the intramedullary nail, a second radially expandable section provided in the distal section adjacent to the tip of the intramedullary nail and a non-expandable middle section provided between said two radially expandable sections of the intramedullary nail. The head may provide a distraction mechanism, by means of which said two radially expandable sections are distractible transverse to said longitudinal axis.

In a preferred embodiment of the intramedullary nail, the non-expandable section of the intramedullary nail may have a length in the range of about 10 mm to about 25 mm, preferably in the range of about 15 mm to about 22 mm. Furthermore, the intramedullary nail may consist of a solid nail core with a head and a tip. In the proximal section adjacent to the head a thread may be provided. The middle section of the core may be configured with a smaller diameter than the end section of the core such that the middle section and the end section are separated by an annular abutment. Apart from the core, the intramedullary nail in one embodiment may comprise: two longitudinally slotted tubular pieces that provide first and second radially expandable sections; two unslotted tubular pieces; and, a nut.

These elements may be slid over the core in the following sequence: a slotted tubular piece; an unslotted tubular piece; a slotted tubular piece; and, an unslotted tubular piece such that adjacent to the tip of the nail a first slotted tubular piece might be provided. The second slotted tubular piece may be separated from the first one by means of an unslotted tubular piece. For instance, adjacent to the end of the nail a nut with an interior thread corresponding to a thread on the core may be mounted to compress the tubular pieces along the longitudinal axis. When these element are aligned on the core a screwing of the nut onto the thread on the core—by means of a driving means such as a spanner, wrench or similar tool engaged to suitable means at the nut such as two parallel sides, hexagonal sides, a hexagon socket or the like—and holding up the core against rotation—by means of a second tool inserted into corresponding suitable means at the core such as a slot, hexagon socket or the like—may produce an axial force or compression on the tubular pieces as the first slotted tubular piece abuts against the abutment of the core and the nut is tightened. Under that compression force the belts between the cuts at the slotted tubular pieces may begin to buckle and deform radially, causing a radial expansion of the slotted tubular pieces. By this effect the nail may expand at a first radially expandable section in the proximal section adjacent to the head of the nail and in a second radially expandable section in the distal section adjacent to the tip of the nail.

Another embodiment of the intramedullary nail may have, instead of the core, a hollow cylindrical or prismatical sleeve extending along the longitudinal axis and surrounding a rodlike locking element coaxially to the longitudinal axis. The locking element may comprise a shaft with a thread in the proximal section towards the head of the nail and a projection forming an abutment in the distal section. In the distal section the sleeve may provide a slot penetrating the side wall through to the bore such that the projection of the locking element may slide within the slot in the direction of the longitudinal axis. Once the tubular elements are aligned on the sleeve as mentioned above the tightening of the nut on the thread on the locking element while holding up the locking element against rotation may cause a compression force onto the tubular elements clamped between the nut and the abutment producing the same effect as described in the above embodiment of the intramedullary nail.

A third preferred embodiment of the intramedullary nail may comprise five elements: a nut; a hollow proximal section; a hollow middle section; a hollow distal section; and, a central wire. Contact between the proximal section and the middle section may be represented by first abutments transversely arranged relative to the longitudinal axis while contact between the middle section and the distal section may be represented by second abutments transversely arranged relative to the longitudinal axis. The central wire may be fixed in the distal section and run through a hollow channel of the other sections. At the proximal end of the nail the central wire may provide threads which correspond to the interior threads of the nut.

When the nut is tightened a sliding of the proximal section and distal section on the first and second transverse abutments respectively may be produced. If the intramedullary channel of the femur has a larger interior diameter than the intramedullary nail, the proximal section and distal section may expand transversely to the longitudinal axis until fixation of the bone fragments may be achieved. This radial expansion may be possible because the first and second transverse abutments may enclose an angle of between about 5° and 85° with the longitudinal axis, and applying a force in the axial direction by means of tightening the nut may cause the proximal section, the middle section and the distal section to move or slide on the abutments providing a sliding component generally orthogonal to the longitudinal axis which may cause a radial expansion of the intramedullary nail. Additionally, the middle section may provide sharp radial teeth which may prevent axial displacement of the bone fragments after fixation of the nail.

In yet another embodiment, the intramedullary nail may comprise three elements: a nut with a head and a conical tip; a central wire with a cone like distal end; and, a hollow intramedullary nail. The ends of the intramedullary nail may be provided with a plurality of cuts which may form contact studs that are radially expandable within the intramedullary channel of the bone. The central wire may run through the hollow channel of the intramedullary nail and—at its proximal end—may have threads which correspond to the interior threads of the nut. When the nut is tightened the distance between the conical tip of the nut and the cone like distal end of the central wire may be shortened, so that the contact studs of the intramedullary nail are expanded by means of the radial forces caused by the axial displacement of the cones. This expansion of the intramedullary nail proximally and distally may produce fixation of the bone fragments of a long bone such as a femur.

In general, an exemplary embodiment of the intramedullary nail for fixation of bone fractures may have a head, a tip and a longitudinal axis, characterized in that: a first radially expandable section may be provided in the proximal section adjacent to the head of the intramedullary nail; a second radially expandable section may be provided in the distal section adjacent to the tip of the intramedullary nail; and a non-expandable middle section may be provided between two radially expandable sections of the intramedullary nail. The exemplary embodiment may further be characterized in that the head may be provided with a distraction mechanism, by means of which two radially expandable sections are distractible transverse to the longitudinal axis of the device.

Another exemplary embodiment may be characterized in that the intramedulary nail comprises a core and at least two slotted tubular pieces that provide the first and second radially expandable sections. The intramedullary nail also may be characterized in that the core provides a middle section—with a minor diameter—and a an end section adjacent to the tip—with a larger diameter—whereby these two sections are separated by an annular abutment. The intramedullary nail may be further characterized in that the slotted tubular pieces are configured slidable on the middle section and prevented from sliding on the end section towards the tip by means of the annular abutment.

In another embodiment of the intramedullary nail, the nail may be characterized in that it comprises at least one unslotted tubular piece providing the non-expandable middle section. The intramedullary nail may be characterized in that the distraction mechanism comprises a thread on the core adjacent to the head and a nut with an interior thread corresponding with thread. For example, the intramedullary nail may be characterized in that said non-expandable section of the intramedullary nail has a length in the range of 10 mm to 25 mm. In another example, the intramedullary nail may be characterized in that said non-expandable section of the intramedullary nail has a length in the range of 15 to 22 mm.

In another embodiment, the intramedullary nail may be characterized in that the tubular pieces are slid over the core in the sequence: a slotted tubular piece, an unslotted tubular piece, a slotted tubular piece and an unslotted tubular piece and at last the nut is screwed over the thread. The intramedullary nail may be further characterized in that the nut comprises means for engagement of a driving means. The intramedullary nail may also be characterized in that the core comprises means for engagement of a holding means. The intramedullary nail also may be characterized in that the means for engagement of a driving means are hexagonal sides. Another embodiment of the intramedullary nail may be characterized in that the means for engagement of a holding means is a slot.

In another embodiment, the intramedullary nail may be characterized in that it comprises a hollow sleeve extending along the longitudinal axis and surrounding a locking element coaxially to the longitudinal axis. The intramedullary nail may be characterized in that the locking element comprises a shaft with a thread in the proximal section and in the distal section a projection forming an abutment. The intramedullary nail may further be characterized in that in the distal section the sleeve provides a slot penetrating the side wall through to the bore such that the projection of the locking element may slide within said slot in the direction of the longitudinal axis.

In another embodiment, the intramedullary nail may be characterized in that it further comprises at least two slotted tubular pieces that provide the first and second radially expandable sections. Additionally, the intramedullary nail may be characterized in that the slotted tubular pieces are configured slidable on the sleeve and prevented from sliding on the end section towards the tip by means of the abutment. The intramedullary nail may also be characterized in that it comprises at least one unslotted tubular piece providing the non-expandable middle section.

In another embodiment the intramedullary nail may be characterized in that the distraction mechanism comprises a thread on the locking element adjacent to the head and a nut with an interior thread corresponding with thread. The intramedullary nail may also be characterized in that the nut comprises means for engagement of a driving means.

In another embodiment, the intramedullary nail may be characterized in that the locking element comprises means for engagement of a holding means. In addition, the intramedullary nail may be characterized in that the distraction mechanism comprises a thread on the locking element adjacent to the head and an end cap with an interior thread corresponding with the thread. The intramedullary nail may be characterized in that the end cap comprises means for engagement of a driving means. The intramedullary nail may be characterized in that the locking element comprises means for engagement of a holding means. The intramedullary nail may be characterized in that it comprises a nut, a hollow proximal section, a hollow middle section, a hollow distal section, and a central wire 54, whereby: contact between the proximal section and the middle section may be represented by transverse abutments (relative to the longitudinal axis 3); contact between middle section and distal section is represented by transverse abutments (relative to the longitudinal axis 3); the central wire may be fixed in the distal section and may run through the hollow channel of sections; at its proximal end the central wire may have threads which correspond to the interior threads of the nut; and the transverse abutments are configured at an angle of between 0.1° and 89.9° with the longitudinal axis such that upon applying a force in the axial direction by means of tightening the nut the proximal section, the middle section and the distal section also provide a sliding component orthogonally to the longitudinal axis on the abutments.

In another embodiment, the intramedullary nail may be characterized in that the middle section provides sharp radial teeth preventing axial displacement of the bone fragments after its fixation. The intramedullary nail also may be characterized in that the distraction mechanism comprises a thread on the wire adjacent to the head and the nut with an interior thread corresponding with the thread. The intramedullary nail may be characterized in that the nut comprises means for engagement of a driving means. Additionally, the intramedullary nail may be characterized in that the wire comprises means for engagement of a holding means when the nut is tightened.

In another embodiment, the intramedullary nail may be characterized in that it comprises a nut with head and conical tip, a central wire with a cone like distal end and a hollow intramedullary nail. The intramedullary nail may be further characterized in that the ends of the intramedullary nail are provided with a plurality of cuts while the central wire runs through the hollow channel of the intramedullary nail and— at its proximal end—has threads which correspond to the interior threads of the nut. The intramedullary nail may also be characterized in that the nut comprises means for engagement of a driving means. The intramedullary nail may also be characterized in that the central wire comprises means for engagement of a holding means when the nut is tightened.

While various descriptions of the present invention are described above, it should be understood that the various features can be used singly or in any combination thereof. Therefore, this invention is not to be limited to only the specifically preferred embodiments depicted herein. For instance, other suitable structures for engagement of a holding means such as a hex or other shaped socket or recess may be employed. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An intramedullary nail having a head, a tip, and a longitudinal axis for fixation of a fractured bone having a medullary canal, the intramedullary nail comprising:
   a first radially expandable section adjacent to the head;
   a second radially expandable section adjacent to the tip; and
   a non-expandable section disposed between the first and second radially expandable sections;
   wherein the first and second radially expandable sections each comprise a slotted tubular member.

2. The intramedullary nail of claim 1, wherein the head is provided a distraction mechanism, and the first and second radially expandable sections are distractible transverse to said longitudinal axis.

3. The intramedullary nail of claim 1, wherein the non-expandable section has a length in the range of about 10 mm to 25 mm.

4. The intramedullary nail of claim 1, wherein the slotted tubular members are configured to be slidable on the sleeve.

5. The intramedullary nail of claim 1, wherein the non-expandable section comprises one unslotted tubular member.

6. The intramedullary nail of claim 5, wherein the non-expandable section of the intramedullary nail has a length in the range of about 15 mm to about 22 mm.

7. The intramedullary nail of claim 1, further comprising a hollow cylindrical sleeve extending along the longitudinal axis and surrounding a locking element coaxially to the longitudinal axis.

8. The intramedullary nail of claim 7, wherein the locking element comprises a shaft with a thread in a proximal section and a projection forming an abutment in the a distal section.

9. The intramedullary nail of claim 7, wherein the sleeve comprises means for engagement of a holding means.

10. The intramedulllary nail of claim 9, wherein the means for engagement of a holding means is a slot.

11. The intramedullary nail of claim 7, wherein the head is provided with a distraction mechanism comprising a thread on the locking element adjacent to the head and a nut with an interior thread corresponding with the thread on the locking element.

12. The intramedullary nail of claim 11, wherein the nut comprises means for engagement of a driving means.

13. The intramedullary nail of claim 7, wherein the locking element comprises means for engagement of a holding means.

14. The intramedullary nail of claim 13, wherein the head is provided with a distraction mechanism comprising a thread on the locking element adjacent to the head and an end cap with an interior thread corresponding with the thread on the locking element.

15. The intramedullary nail of claim 14, wherein the end cap comprises means for engagement of a driving means.

16. An intramedullary nail having a head, a tin, and a longitudinal axis for fixation of a fractured bone having a medullary canal, the intramedullary nail comprising:

a first radially expandable section adjacent to the head;

a second radially expandable section adjacent to the tip; and a non-expandable section disposed between the first and second radially expandable sections;

wherein the expandable and non-expandable sections are tubular members that are positioned over the sleeve in sequence and are secured on the sleeve by a nut, the sequence of positioning the tubular members comprising: a slotted tubular member, an unslotted tubular member, a slotted tubular member, and an unslotted tubular member.

17. The intramedullary nail of claim 16, wherein the nut comprises means for engagement of a driving means.

18. The intramedullary nail of claim 17, wherein the means for engagement of a driving means comprises hexagonal sides.

19. An intramedullary nail having a head, a tip, and a longitudinal axis for fixation of a fractured bone having a medullary canal, the intramedullary nail comprising:

a first radially expandable section adjacent to the head;

a second radially expandable section adjacent to the tip;

a non-expandable section disposed between the first and second radially expandable sections; and a hollow cylindrical sleeve extending along the longitudinal axis and surrounding a locking element coaxially to the longitudinal axis;

wherein the locking element comprises a shaft with a thread in a proximal section and a projection forming an abutment in a distal section; and wherein a distal section of the sleeve provides a slot penetrating a side wall through to a bore and the projection of the locking element is movable to slide within said slot in the direction of the longitudinal axis.

20. An intramedullary nail for fixation of a fractured bone having a medullary canal, the intramedullary nail comprising:

a central member comprising a proximal section with a head, a distal section with a tip, and a longitudinal axis;

a first radially expandable member slidably disposed on the proximal section of the central member;

a second radially expandable member slidably disposed on the distal section of the central member; and a non-expandable section slidably disposed on the central member between the first and second radially expandable sections.

21. The intramedullary nail of claim 20, wherein the first and second radially expandable sections each comprise a slotted tubular member.

22. The intramedullary nail of claim 20, wherein the head is provided with a distraction mechanism, and the first and second radially expandable sections are distractible with respect to each other.

23. The intramedullary nail of claim 20, wherein the non-expandable section comprises at least one unslotted tubular member.

24. The intramedullary nail of claim 20, wherein the non-expandable section has a length in the range of about 10 mm to 25 mm.

25. The intramedullary nail of claim 20, wherein the non-expandable section has a length in the range of about 15 mm to about 22 mm.

26. The intramedullary nail of claim 20, wherein the head is provided with a distraction mechanism comprising a threaded portion and a nut threadably associated therewith.

27. The intramedullary nail of claim 26, wherein the nut comprises means for engagement of a driving means.

28. The intramedullary nail of claim 20, further comprising a hollow cylindrical sleeve disposed about the longitudinal axis and surrounding a shaft comprising a thread in a proximal section and a projection forming an abutment in the distal section.

29. The intramedullary nail of claim 28, wherein a distal section of the sleeve comprises a slot extending to a bore therein an the projection of the shaft is slidable within the slot in the direction of the longitudinal axis.

30. The intramedullary nail of claim 20, further comprising a hollow cylindrical sleeve extending about the longitudinal axis and surrounding a locking element.

31. The intramedullary nail of claim 30, wherein the expandable and non-expandable sections are tubular members that are disposed on the sleeve in sequence and are secured on the sleeve by a nut, the sequence comprising: a slotted tubular member, an unslotted tubular member, and a slotted tubular member.

32. The intramedullary nail of claim 31, wherein the nut comprises means for engagement of a driving means.

33. The intramedullary nail of claim 32, wherein the means for engagement of a driving means comprises hexagonal sides.

* * * * *